United States Patent
Neame

(10) Patent No.: US 9,072,858 B2
(45) Date of Patent: Jul. 7, 2015

(54) MEDICAL TUBE ASSEMBLIES

(75) Inventor: Simon Neame, Broadstairs (GB)

(73) Assignee: Smiths Group PLC, London (GB)

(*) Notice: Subject to any disclaimer, the term of this patent is extended or adjusted under 35 U.S.C. 154(b) by 2283 days.

(21) Appl. No.: 12/003,003

(22) Filed: Dec. 19, 2007

(65) Prior Publication Data
US 2008/0149108 A1    Jun. 26, 2008

(30) Foreign Application Priority Data

Dec. 21, 2006    (GB) .................................... 0625575.6

(51) Int. Cl.
*A61M 16/04*    (2006.01)
*A61M 16/08*    (2006.01)

(52) U.S. Cl.
CPC ........... *A61M 16/08* (2013.01); *A61M 16/0816* (2013.01); *A61M 16/0465* (2013.01); *A61M 16/0427* (2014.02)

(58) Field of Classification Search
CPC . A61M 16/10; A61M 16/04; A61M 16/0465; A61M 16/0427; A61M 16/0497; A61M 16/0468; A61M 16/0429; A61M 16/1045; A61M 16/08; A61F 2/20; A61F 2/203; B01D 39/18; B01D 39/16; B01D 39/20; B01D 39/1623; B01D 39/2055
USPC ............. 128/200.24, 200.26, 207.14–207.18; 604/101.01, 164.01–164.09, 174
See application file for complete search history.

(56) References Cited

U.S. PATENT DOCUMENTS

| | | | |
|---|---|---|---|
| 2,786,469 A | 3/1957 | Cohen | |
| 3,039,469 A | 6/1962 | Fountain | |
| 3,169,529 A * | 2/1965 | Koenig | 128/207.14 |
| 3,659,612 A * | 5/1972 | Shiley et al. | 128/207.15 |
| 3,688,774 A | 9/1972 | Akiyama | |
| 4,033,353 A * | 7/1977 | La Rosa | 128/207.15 |
| 4,304,228 A * | 12/1981 | Depel | 128/200.26 |
| 4,449,523 A * | 5/1984 | Szachowicz et al. | 128/200.26 |
| 5,056,515 A * | 10/1991 | Abel | 128/207.15 |
| 5,460,176 A * | 10/1995 | Frigger | 128/207.14 |
| 5,606,966 A * | 3/1997 | Smith | 128/200.26 |

FOREIGN PATENT DOCUMENTS

| | | |
|---|---|---|
| DE | 20 2004 007 251 | 8/2004 |
| EP | 1 520 599 | 4/2005 |
| WO | 2007/038562 | 4/2007 |

* cited by examiner

*Primary Examiner* — Annette Dixon
(74) *Attorney, Agent, or Firm* — Louis Woo

(57) ABSTRACT

A tracheostomy tube assembly comprises an outer tube and an inner cannula. The machine end fitting of the outer tube has a bore of circular section interrupted by two flats. The machine end fitting of the inner cannula has an external surface shaped to fit within the fitting on the outer tube and also has two flats aligned with the flats on the outer tube fitting. Tubes of different sizes or other characteristics have flats with different orientations such that only inner cannulae suited for a particular outer tube can be inserted in the correct tube.

3 Claims, 4 Drawing Sheets

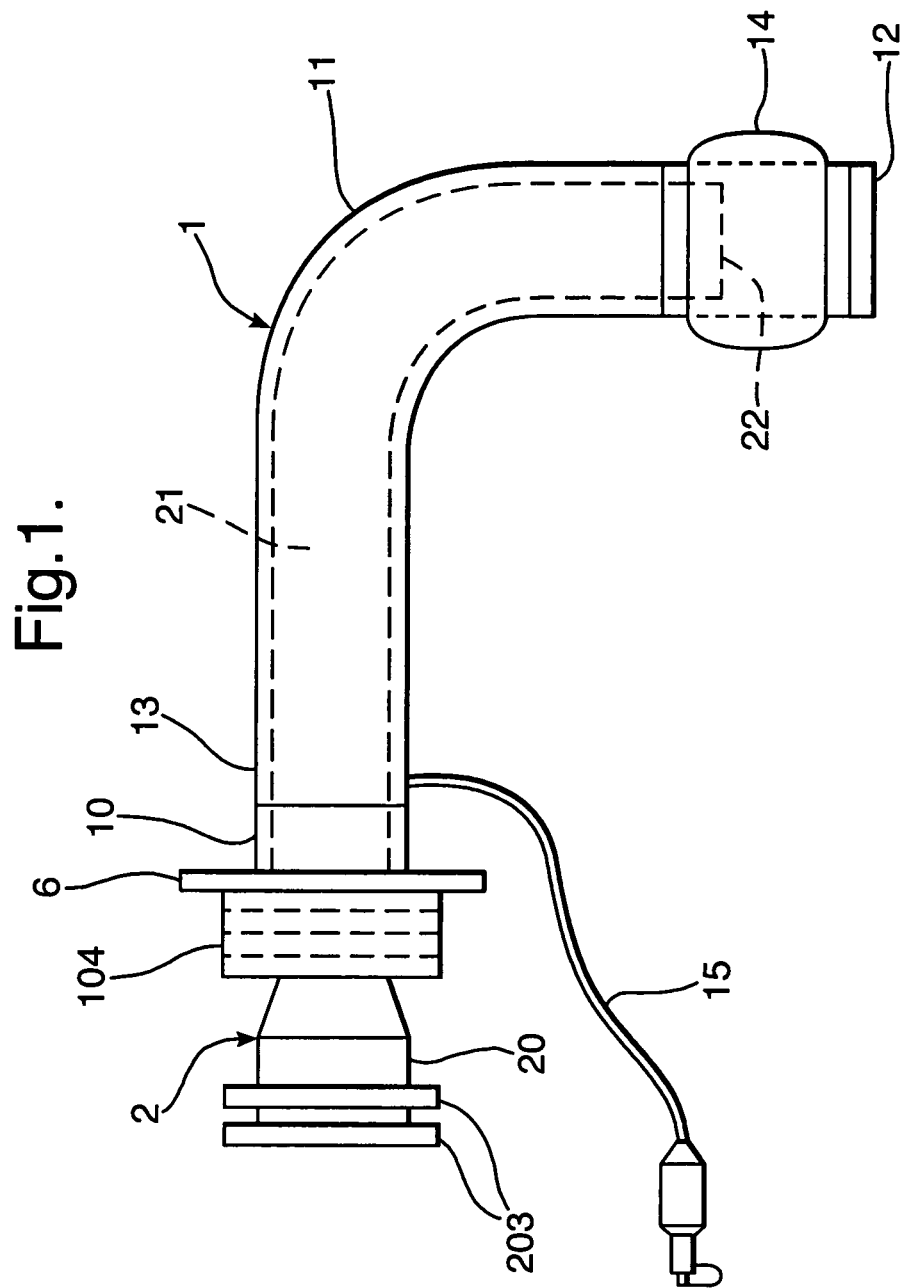

MEDICAL TUBE ASSEMBLIES

CROSS REFERENCE TO RELATED APPLICATION

This application claims foreign priority of UK application GB 0625575.6 filed Dec. 21, 2006.

BACKGROUND OF THE INVENTION

This invention relates to medical tube assemblies.

The invention is more particularly concerned with tube assemblies of the kind comprising an outer tube and an inner tube insertable into and removable from the machine end of the outer tube.

Tracheostomy tubes are often provided with a removable inner cannula. When secretions accumulate inside the assembly, the inner cannula can be removed and replaced. This avoids the need to replace the outer tube, which would be more traumatic and would have to be carried out by a doctor. Tracheostomy tubes are provided in a range of different characteristics for use in different situations. For example, the tubes can be made of different materials, different shapes, can be reinforced or unreinforced or can be of different sizes. Also, in a hospital, tubes may be available from different manufacturers. The outer tubes of different characteristics require different size inner cannulae. There is a risk, with conventional assemblies, that a nurse or other practitioner could replace an inner cannula with a cannula of the wrong characteristic or type. For example, an inner cannula intended for use in a reinforced outer tube might be wrongly inserted in an unreinforced tube. This could cause a poor fit or damage to the inner cannula or outer tube.

BRIEF SUMMARY OF THE INVENTION

It is an object of the present invention to provide an alternative medical tube assembly.

According to one aspect of the present invention there is provided a medical tube assembly comprising an outer tube and an inner tube insertable into and removable from a machine end of said outer tube, the outer tube and the inner tube having cooperable machine end fittings of non-circular section, and the machine end fittings being adapted to fit with one another and to restrict insertion of inner tubes having different machine end fittings.

The machine end fitting on the outer tube preferably has an inner surface of circular section interrupted by two or more flats spaced from one another, the machine end fitting on the inner tube having an outer surface of circular section interrupted by two or more flats arranged to align with the flats on the fitting of the outer tube. The flats in the machine end fitting of the outer tube preferably extend along the length of the bore of the fitting. The outer tube is preferably a tracheostomy tube.

According to another aspect of the present invention there is provided a tracheostomy tube assembly comprising an outer tracheostomy tube and an inner cannula insertable into and removable from a machine end of said tracheostomy tube, the tracheostomy tube and said inner cannula having cooperable machine end fittings with the machine end fitting of the tracheostomy tube having an inner surface of circular section interrupted by at least two flats, and the machine end fitting of the inner cannula has an external surface of circular section interrupted by the same number of flats arranged to align with the flats on the machine end fitting of the tracheostomy tube such that inner cannulae with different machine end fittings are restricted from fitting with the tracheostomy tube.

According to a third aspect of the present invention there is provided a system comprising a plurality of medical outer tubes of different characteristics and a plurality of different inner tubes arranged to be insertable within and removable from respective ones of the outer tubes, the outer tubes of different characteristics having machine end fittings different from one another, and different ones of the inner tubes having machine end fittings different from one another such that the machine end fittings of the inner tubes can only be fully inserted in machine end fittings of the outer tubes of a corresponding characteristic.

The machine end fitting on each outer tube preferably has an inner surface of circular section interrupted by two or more flats spaced from one another, the disposition of the flats being different on tubes of different characteristics, the machine end fitting on each inner tube having an outer surface of circular section interrupted by two or more flats, and the disposition of the flats being different on inner tubes of different characteristics such that they align only with the flats on the fittings of outer tubes of the corresponding characteristic. The flats in the machine end fitting of each outer tube preferably extend along the length of the bore of the fitting.

According to a further aspect of the present invention there is provided a method of maintaining a tracheostomy tube assembly located in a patient, the assembly including an outer tube and an inner cannula removable from the outer tube, including the steps of periodically removing and disposing of the inner cannula while leaving the outer tube in position, selecting a replacement inner cannula from a group of cannulae having differently-shaped machine end fittings to be compatible with a machine end fitting on the outer tube, and inserting the inner cannula in the outer tube.

The machine end fitting on the outer tubes and the machine end fitting on the inner cannulae preferably have a circular section interrupted by two or more spaced flat surfaces, and the flat surfaces on outer tubes and inner cannulae of different characteristics are preferably at different dispositions such that an inner cannula can only be fully inserted within an outer tube of the correct characteristics.

A tracheostomy assembly and its method of maintenance, according to the present invention, will now be described, by way of example, with reference to the accompanying drawings.

BRIEF DESCRIPTION OF THE DRAWINGS

FIG. 1 is a side elevation view of the tracheostomy tube assembly with the inner cannula not quite fully inserted;

DETAILED DESCRIPTION OF THE PREFERRED EMBODIMENT

Figure 2A:
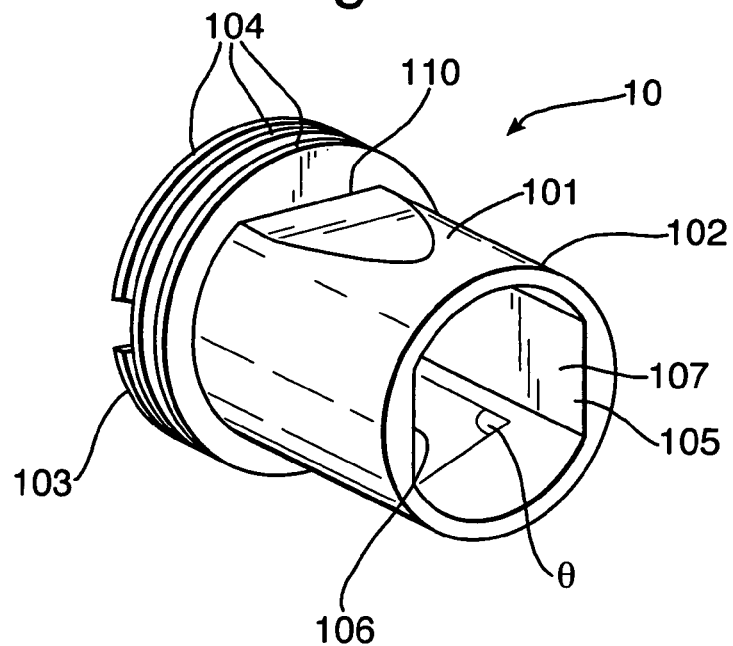
FIGS. 2A and 2B are perspective views of the forward end of the machine end fittings of the outer tube and inner cannula respectively.
Figure 2B:
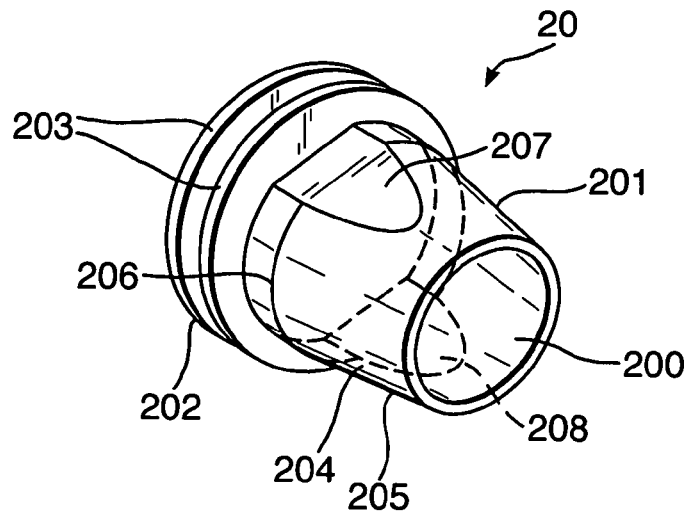

With reference to FIGS. 1, 2A and 2B, the tracheostomy tube assembly comprises an outer tube 1 and an inner tube or cannula 2, which is insertable into and removable from the outer tube. The machine end fittings 10 and 20 on the outer tube and inner cannula are shaped so that only an inner cannula 2 of the appropriate characteristic can be fully inserted into the outer tube 1.

The outer tube 1 comprises a curved tubular shaft 11 extending from a forward, patient end 12, adapted to be located in the trachea, to a rear, machine end 13, adapted to be located outside the trachea. The shaft 11 may be curved continuously along its length instead of having the straight, bend, straight shape shown in FIG. 1. Alternatively, the shaft could have a natural straight shape and be highly bendable. The shaft 11 may be made of any conventional material, such as PVC, polyurethane, silicone or even metal. Where the shaft is of a plastics material it could be reinforced with a helical wire embedded in the wall of the shaft. The tube 1 has an inflatable sealing cuff 14 extending around the shaft 11 close to the patient end 12; this is inflatable and deflatable via an inflation line 15 in the usual way. Close to its machine end 13, the tube 1 has a neck flange 6 positioned to lie against the skin of the neck around the tracheostomy. The flange 6 has apertures or the like (not visible) to which a tape extending around the patient's neck can be attached. This is used to secure the flange 6 in position and stabilize the tube assembly.

The machine end fitting 10 is shown most clearly in FIG. 2A and is shown before being moulded onto the flange 6 and the shaft 11. It is a tubular component moulded from a rigid plastics material such as polypropylene or polysulphone. The fitting 10 has an external surface 101 of circular section with integral ribs 110 for attachment to the flange 6 by overmoulding. The forward end 102 of the fitting 10 is bonded with the machine end of the shaft 11. It will be appreciated that the fitting 10, and that on the inner cannula 20, need not be formed separately of the shaft 11 but could be a unitary, integral part of the shaft. The rear end 103 of the fitting 10 is moulded with three radially-projecting annular ribs 104, about which the flange 6 is moulded. Inside the fitting 10, an axial bore 105 extends along its length to form a continuation of the bore along the shaft 11. The bore 105 tapers slightly along the length of the fitting 10 so that it has a slightly larger diameter at its forward, patient end. The bore 105 has a circular section interrupted by two flat surfaces or flats 106 and 107 extending longitudinally along the entire length of the bore. The flats 106 and 107, in the present example, are disposed diametrically opposite one another, so that their surfaces are parallel with each other. The width of the flats 106 and 107 is such that they each subtend an angle θ of 30° at the centre of the fitting. It will be appreciated that there could be more than two flats.

The inner cannula 2 comprises a thin-walled tubular shaft 21 of circular section extending forwardly from the machine end fitting 20. The shape and dimensions of the shaft 21 are selected so that it is a close fit within the bore of the shaft 11 of the outer tube 1, so that it can be inserted freely within the outer tube without buckling. Its patient end 22 lies close to the patient end 12 of the outer tube 1 without protruding therefrom when fully inserted. The machine end fitting 20 of the inner cannula 2 is shown most clearly in FIG. 2B. It is a tubular component moulded from a rigid plastics material such as polyethylene or ePTFE. The fitting 20 has an axial bore 200 extending along its length from the forward, patient end 201 of the fitting to its rear end 202. The bore 200 has a circular section of constant diameter along its length. The forward end 201 of the fitting 20 is bonded with the machine end of the shaft 21. The rear end 202 of the fitting 20 is moulded with two radially-projecting annular ribs 203, which together act as a finger grip. The external surface 204 of the fitting 20 has a forward tapering section 205 and a rear section 206 of constant diameter. The external surface 204 has a circular section interrupted by two flat surfaces 207 and 208 formed on the rear section 206 and extending along a part of the length of the tapering section 205. The flats 207 and 208 extend longitudinally and, in this example, are disposed diametrically opposite one another on opposite sides of the fitting. More particularly, the external shape and dimensions of the machine end fitting 20 on the inner cannula 2 are arranged so that the fitting fits snugly within the machine end fitting 10 on the outer tube, when the respective flats 207, 208 and 106, 107 are aligned with one another. The cooperating machine end fittings on the inner cannula and the outer tube may have cooperating detents (not shown) to retain the inner cannula within the outer tube during normal use, until the clinician grips the finger grip at the end of the inner cannula and pulls it out of the outer tube for replacement.

The tracheostomy tube assembly described above forms a part of a system of a range of tracheostomy tube assemblies of different characteristics for use on different patients in different situations. The outer tubes may be of different materials, shapes, reinforcement characteristics and sizes. There is a range of corresponding inner cannulae to fit corresponding ones of the outer tubes. The machine end fittings of the different outer tubes and inner cannulae are shaped differently so that only the appropriate inner cannula can be fully inserted within a particular outer tube. The machine end fittings of the outer tubes and inner cannula of different characteristics are colour coded or otherwise visibly marked so that it is clear which inner cannula is for which outer tube.

Figure 3A:
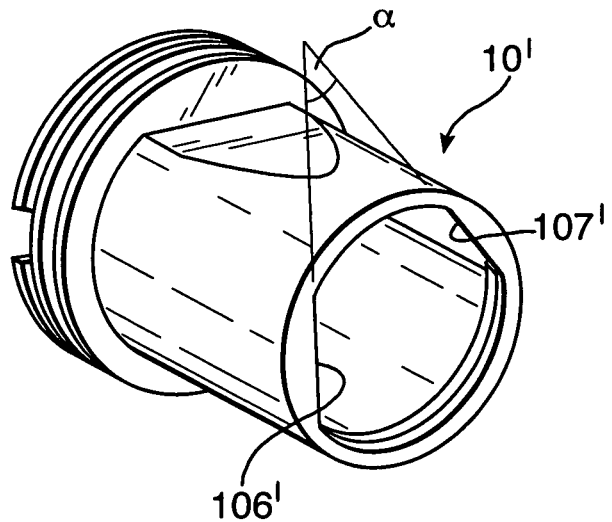
FIGS. 3A and 3B are perspective views of the forward end of machine end fittings of an outer tube and inner cannula of different size.
Figure 3B:
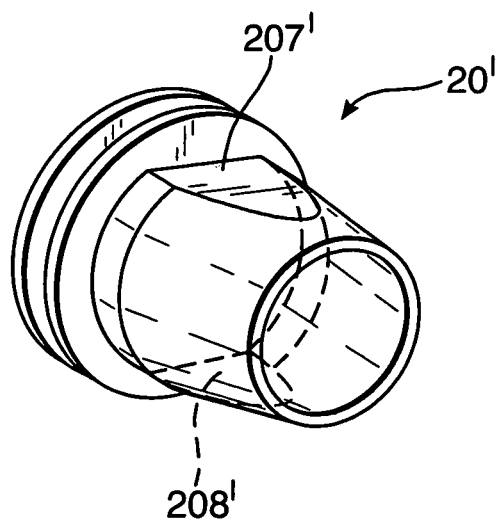

FIGS. 3A and 3B show machine end fittings 10' and 20' for a different outer tube and inner cannula respectively. The fittings 10' and 20' are the same as those shown in FIGS. 2A and 2B except for the disposition of the flats 106' and 107' in the outer tube fitting and the flats 207' and 208' in the inner cannula fitting. Instead of being arranged parallel to one another, the flats 106' and 107' are located to lie at an angle α of 30° with respect to one another. Similarly, the flats 207' and 208' on the machine end fitting 20' of the inner cannula are disposed at the same angle of 30° so that they align with the flats 106' and 107' when the inner cannula fitting is presented up to the fitting 10' on the outer tube.

Figure 4A:
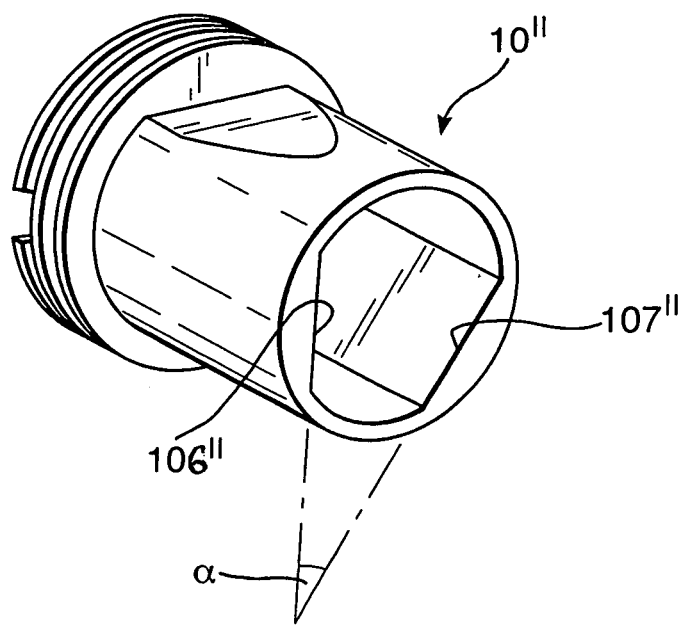
FIGS. 4A and 4B are perspective views of the forward end of machine end fittings of an outer tube and inner cannula of another different size.
Figure 4B:
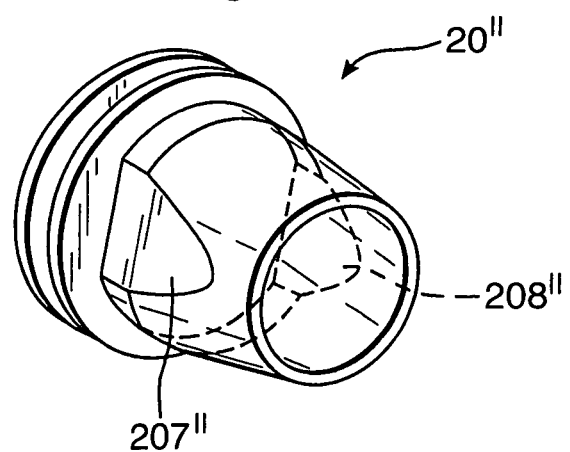

FIGS. 4A and 4B show machine end fittings 10" and 20" for an outer tube and inner cannula having a third different characteristic. In this case, the flats 106" and 107" on the outer tube fitting 10" are inclined at an angle α of 45° with respect to one another and the flats 207" and 208" on the inner cannula fitting 20" are similarly aligned at the same angle.

In use, when the nurse or other clinician determines that the tracheostomy tube needs cleaning, he pulls out the inner cannula 2 by gripping its finger grip 203 with one hand while stabilising the tube 1 with the other hand. He disposes of the old inner cannula 2 and selects a new, replacement inner cannula from a range of cannulae of different characteristics confirming that it is the correct cannula by checking any markings on the cannula or packaging and by checking the colour-coded machine end fitting. He then inserts the patient end 12 of the inner cannula 2 into the machine end 13 of the outer tube 1 and threads it in forwardly until the machine end 20 fitting on the inner cannula 2 comes close to the machine end fitting 10 on the outer tube 1. He then aligns the machine end fittings 10 and 20 so that the flats 106, 107 and 207, 208 on the two fittings align with one another. Preferably, the two machine end fittings 10 and 20 are provided with suitable angular alignment markers (not shown) to facilitate alignment. If the correct inner cannula 2 has been selected, the machine end fitting 20 on the inner cannula will slide snugly into the fitting 10 on the outer tube 1 and the finger grip 203 on the inner cannula will abut that 104 on the outer tube when the inner cannula has been fully inserted. If, however, the wrong inner cannula should be selected inadvertently, the flats on the two fittings would not align and it would be impossible easily to insert the inner cannula fully into the outer tube. This would be immediately apparent to the clinician thereby prompting him to select a different cannula having the correct characteristics.

The invention also has the advantage of preventing use of an inner cannula in an incompatible outer tube of different characteristics. This could be a tube from a different manufacturer, or from the same manufacturer but in a different range (such as reinforced and unreinforced), or a tube of different size. Because the flats extend along the length of the bore of the machine end fitting they ensure that the inside of the fitting can be cleaned easily and the internal geometry of the end fitting does not have any crevices or recesses in which secretions could collect. This is preferable to a key arrangement having a key aperture at the machine end only of the fitting, which would provide a possible trap behind the key aperture in which secretions could collect.

It will be appreciated that the invention is not confined to tracheostomy tubes but could be used in any other medical tube having an inner tube or cannula. Furthermore, the machine end fittings need not be used to restrict use of inner and outer tubes with one another according to their size but could be used with ranges of tubes having other different characteristics within the range, such as, material, shape, function or the like.

What I claim is:

1. A system comprising a plurality of outer tracheal tubes of different characteristics and a plurality of different inner tubes arranged to be insertable within and removable from respective ones of the outer tubes, the inner tubes having a machine end fitting and a shaft adapted to extend forwardly from the machine end fitting along the length of the respective outer tubes, wherein the machine end fittings of outer tubes of different characteristics are different from one another, wherein the machine end fittings of the different inner tubes are different from one another such that the machine end fittings of the inner tubes can only be fully inserted in machine end fittings of the outer tubes of a corresponding characteristic, wherein the machine end fitting on each outer tube has an inner surface of circular section interrupted by two or more flats spaced from one another, that the disposition of the flats is different on tubes of different characteristics, wherein the machine end fitting on each inner tube has an outer surface of circular section interrupted by two or more flats, and wherein the disposition of the flats is different on inner tubes of different characteristics such that they align only with the flats on the fittings of outer tubes of the corresponding characteristic.

2. A system according to claim 1, wherein said outer tube is a tracheostomy tube.

3. A method of maintaining a tracheostomy tube assembly located in a patient, the assembly including an outer tube and an inner cannula removable from the outer tube, including the steps of periodically removing and disposing of the inner cannula while leaving the outer tube in position, selecting a replacement inner cannula from a group of cannulae having differently-shaped machine end fittings to be compatible with a machine end fitting on the outer tube, and inserting the inner cannula in the outer tube, wherein the machine end fitting on the outer tubes and the machine end fitting on the inner cannulae have a circular section interrupted by two or more spaced flat surfaces, and wherein the flat surfaces on outer tubes and inner cannulae of different characteristics are at different dispositions such that an inner cannula can only be fully inserted within an outer tube of the correct characteristics.

* * * * *